US010441627B2

(12) United States Patent
Danglas et al.

(10) Patent No.: US 10,441,627 B2
(45) Date of Patent: Oct. 15, 2019

(54) METHOD OF TREATING PRADER-WILLI SYNDROME

(71) Applicant: Ferring B.V., Hoofddorp (NL)

(72) Inventors: Pascal Danglas, Ollon (CH); Michael Reidy, Kinnelon, NJ (US); Paul Korner, Franklin Lakes, NJ (US); Sudarkodi Alagarsamy, Millburn, NJ (US)

(73) Assignee: FERRING B.V., Hoofddorp (NL)

( * ) Notice: Subject to any disclaimer, the term of this patent is extended or adjusted under 35 U.S.C. 154(b) by 0 days.

(21) Appl. No.: 15/510,781

(22) PCT Filed: Sep. 14, 2015

(86) PCT No.: PCT/US2015/049911
§ 371 (c)(1),
(2) Date: Mar. 13, 2017

(87) PCT Pub. No.: WO2016/044131
PCT Pub. Date: Mar. 24, 2016

(65) Prior Publication Data
US 2017/0326200 A1   Nov. 16, 2017

Related U.S. Application Data

(60) Provisional application No. 62/052,957, filed on Sep. 19, 2014.

(51) Int. Cl.
| | | |
|---|---|---|
| *A61K 38/11* | (2006.01) | |
| *A61K 47/00* | (2006.01) | |
| *A61K 9/00* | (2006.01) | |
| *A61K 9/08* | (2006.01) | |
| *A61K 38/095* | (2019.01) | |
| *A61K 47/02* | (2006.01) | |

(52) U.S. Cl.
CPC .......... *A61K 38/095* (2019.01); *A61K 9/0043* (2013.01); *A61K 9/08* (2013.01); *A61K 47/02* (2013.01)

(58) Field of Classification Search
CPC ...... A61K 38/11; A61K 47/02; A61K 9/0043; A61K 9/08
See application file for complete search history.

(56) References Cited

U.S. PATENT DOCUMENTS

| | | | |
|---|---|---|---|
| 6,894,026 B1 | 5/2005 | Quay | |
| 8,853,158 B2 | 10/2014 | Muscatelli et al. | |
| 8,865,746 B2 | 10/2014 | Vath | |
| 9,023,793 B2 | 5/2015 | Leonard et al. | |
| 9,125,862 B2 | 9/2015 | Muscatelli et al. | |
| 9,751,870 B2 | 9/2017 | Bissantz et al. | |
| 9,789,155 B2 | 10/2017 | Young et al. | |
| 2004/0235956 A1* | 11/2004 | Quay | A61K 31/395 514/573 |
| 2007/0032410 A1 | 2/2007 | Quay et al. | |
| 2010/0292437 A1 | 11/2010 | Nelson et al. | |
| 2010/0311655 A1 | 12/2010 | Leonard et al. | |
| 2012/0108510 A1 | 5/2012 | Young et al. | |
| 2013/0102528 A1 | 3/2013 | Muscatelli et al. | |
| 2015/0216835 A1 | 8/2015 | Vath | |
| 2015/0284434 A1 | 10/2015 | Bissantz et al. | |
| 2017/0056364 A1 | 3/2017 | Vath | |
| 2017/0081368 A1 | 3/2017 | Bissantz et al. | |
| 2017/0081369 A1 | 3/2017 | Bissantz et al. | |
| 2017/0174725 A1 | 6/2017 | Bleicher et al. | |

FOREIGN PATENT DOCUMENTS

| | | |
|---|---|---|
| WO | WO 2009/033782 | 3/2009 |
| WO | WO 2009/033783 | 3/2009 |
| WO | WO 2009/033820 | 3/2009 |
| WO | WO 2009/043457 | 4/2009 |
| WO | 2009/122285 | 10/2009 |
| WO | 2011/035330 | 3/2011 |
| WO | WO 2012/149472 | 3/2011 |
| WO | 2011/147889 | 12/2011 |
| WO | 2014/095773 | 6/2014 |
| WO | 2014/111356 | 7/2014 |
| WO | WO 2015/185467 | 12/2015 |
| WO | WO 2015/185584 | 12/2015 |
| WO | WO 2016/020349 | 2/2016 |
| WO | WO 2016/044131 | 3/2016 |

OTHER PUBLICATIONS

Boss et al., "Induction of NFAT-mediated transcription by Gq-coupled receptors in lymphoid and non-lymphoid cells," Biol. Chem., May 1996, 271(18): 10429-10432.
Dykens and Rosner, "Refining behavioral phenotypes: personality-motivation in Williams and Prader-Willi syndromes," Am. J Mental Retardation, Mar. 1999, 104(2):158-169.
Dykens et al., "Assessment of Hyperphagia in Prader-Willi Syndrome," Obesity, Jul. 2007, 15:1816-26.
International Preliminary Report on Patentability in International Application No. PCT/US2015/049911, dated Mar. 30, 2017, 9 pages.
Miller et al, "Nutritional Phases in Prader—Willi Syndrome," Am J Med Genet A, May 2011, 155A(5): 1040-1049.
Scahill, et al., "Children's Yale-Brown Obsessive Compulsive Scale: reliability and validity," J Am Acad ChildAdolesc Psychiatry, Jun. 1997, 36:844-52.
Anonymous: "Treatment of Hyperphagia Behavioral Symptoms in Children and Adults Diagnosed with Prader-Willi Syndrome, Foundation for Prader-Willi Research," May 7, 2014 (URL:http://www.fpwr.org/carbetocin-a-selective-oxytocin-agonist-oxytocin-agonist-in-the-treatment-of-pws/).

(Continued)

*Primary Examiner* — James H Alstrum-Acevedo
*Assistant Examiner* — Erinne R Dabkowski
(74) *Attorney, Agent, or Firm* — Foley & Lardner LLP

(57) ABSTRACT

This disclosure relates to a method of treating Prader-Willi Syndrome. The method includes administering to a patient in need thereof an effective amount of a composition containing a selective oxytocin receptor agonist or a pharmaceutically acceptable salt thereof.

23 Claims, No Drawings
Specification includes a Sequence Listing.

(56) References Cited

OTHER PUBLICATIONS

Anonymous: "Clinical trial: NCT01968187," Aug. 19, 2014 (URL:https://clinicaltrials.gov/archive/NCT01968187/2014_08_19) and Anonymous: "Validation of Analytical Procedure for Carbetocin, FE992097," Sep. 20, 2010 (URL://www.bpfk.gov.my/Biro/508O2-P/790826-14-5054/pharma/S4.3_Dura_ValidAP%200112.pdf).

Einfeld et al., "A double-blind randomized controlled trial of oxytocin nasal spray in Prader Willi syndrome," American Journal of Medical Genetics Part A, vol. 164, No. 9, Jun. 30, 2014 and supplemental information.

Gimple, "Oxytocin receptor ligands. A survey of the patent literature," Expert Opinion on Therapeutic Patents, Informa Halthcare, GB, vol. 18, No. 11, Nov. 1, 2008.

International Search Report of ISA/EP for PCT/US2015/049911, dated Nov. 24, 2015.

Tauber, "Oxytocin may be useful to increase trust in others an decrease disruptive behaviours in patients with Prader-Willi syndrome: a randomized placebo-controlled trial in 24 patients," Orphanet Journal of Rare Diseases 2011, 6:47.

Badiu and Marginean, "Current status and perspectives in the Treatment of Prader-Willi syndrome", Expert Opinion on Orphan Drugs, Apr. 2014, 2(4):337-347.

Bakermans-Kranenburg, et al., "Sniffing around oxytocin: review and meta-analyses of trials in healthy and clinical groups with implications for pharmacotherapy", Translational Psychiatry, 2013, 3:1-14.

Bueno Diez, et al., "Prader-Willi syndrome and hyperphagia: A challenge to investigate", Endocrinol. Nutr., 2014, 61:121-122.

Busner and Targum, "The clinical global impressions scale: applying a research tool in clinical practice." Psychiatry (Edgmont). 20074(7):28-37.

Chapman et al., "Intranasal Treatment of Central Nervous System Dysfunction in Humans", Pharmaceutical Research, Oct. 2013, 30(10):2475-2484.

Deblon, et al., "Mechanisms of the Anti-Obesity Effects of Oxytocin in Diet-Induced Obese Rats", PLoS One, Sep. 27, 2011, 6(9):e25565.

Dutch Growth Research Foundation, "Intranasal administration of oxytocin in children and young adults with Prader-Willi Syndrome. A randomized, double-blind, placebo-controlled trial. Effects on satiety and food intake, and social behaviour", AdisInsight: Trials, Jul. 30, 2014.

De Berardis, et al.., "The Role of Intranasal Oxytocin in the Treatment of Patients with Schizophrenia: A Systematic Review", CNS & Neurological Disorders-Drug Targets, Mar. 2013, 12(2):252-264.

Eiholzer and Whitman, "A Comprehensive Team Approach to the Management of Patients with Prader-Willi Syndrome", Journal of Pediatric Endocrinology and Metabolism, Sep. 2004, 17(9):1153-1175.

EMA,"Public summary of opinion on orphan designation. Carbetocin for the treatment of Prader-Willi syndrome" dated Apr. 4, 2012 from Public summary of opinion on orphan designation EMA/COMP/69949/2012, [retrieved on Jan. 24, 2019]. Retrieved from the Internet: https://www.ema.europa.eu/documents/orphan-designation/eu/3/12/975-public-summary-opinion-orphan-designation-carbetocin-treatment-prader-willi-syndrome_en.pdf.

Goldstone, et al., "Appetite hormones and the transition to hyperphagia in children with Prader-Willi syndrome", International Journal of Obesity, Dec. 2012, 36(12):1564-1570.

Goldstone, "Prader-Willi syndrome: advances in genetics, pathophysiology and treatment", Trends in Endocrinology and Metabolism, Jan. 2004-Feb. 2004, 15(1):12-20.

Harris, et al., "Therapeutic Interventions With Oxytocin: Current Status and Concerns", Journal of the American Academy of Child & Adolescent Psychiatry, Oct. 2013, 52(10):998-1000.

Heymsfield, et al., "Hyperphagia: Current Concepts and Future Directions Proceedings of the 2nd International Conference on Hyperphagia", Obesity, 2014, 22:S1-S17.

Ho, et al., "Coming Full Circle: Contributions of Central and Peripheral Oxytocin Actions to Energy Balance", Endocrinology, Feb. 2013, 154(2):589-596.

Holland, et al., "Understanding the eating disorder affecting people with Prader-Willi syndrome", Journal of Applied Research in Intellectual Disabilities, 1998, 11(3):192-206.

Kelly and Feifel, et al., "Emerging Clinical Evidence on Oxytocin in Schizophrenia (abstract)", Schizophrenia Research, Apr. 2012, 136(Supp. 1):S69.

Manning et al., "Peptide and non-peptide agonists and antagonists for the vasopressin and oxytocin V1a, V1b, V2 and OT receptors: research tools and potential therapeutic agents", Prog Brain Res, 2008, 170:473-512.

Marazziti et al., "The Role of Oxytocin in Neuropsychiatric Disorders", Current Medicinal Chemistry, 2008, 15(7):698-704.

Mcallister, et al., "Development of the eating behaviour in Prader-Willi Syndrome: advances in our understanding", International Journal of Obesity, Feb. 2011, 35(2):188-97.

NewsRx, Chu De Toulouse; Agency Reviews Patent Application Approval Request for "Methods and Pharmaceutical Composition for the Treatment of a Feeding Disorder with Early-Onset in a Patient", Genetics & Environmental Law Weekly May 18, 2013):225, [retrieved on Jul. 7, 2017]. Retrieved from the Internet: https://dialog.proquest.com/professional/docview/1349133491?accountid=156232.

NewsRx, "Clinical Research; Findings in the Area of Clinical Trials and Studies Reported from University of Sydney (A Double-Blind Randomized Controlled Trial of Oxytocin Nasal Spray in Prader Willi Syndrome) (A Double-Blind Randomized Controlled Trial of Oxytocin Nasal . . . )", Biotech Week (Sep. 24, 2014): 481.[retrieved on Jul. 7, 2017]. Retrieved from the Internet: https://dialog.proquest.com/professional/docview/1562469856?accountid=156232.

Onaka, Jichi et al., "Roles of Oxytocin Neurones in the Control of Stress, Energy Metabolism, and Social Behaviour", Journal of Endocrinology, Apr. 2012, 24:587-598.

Olszewski et al., "Oxytocin as Feeding Inhibitor: Maintaining Homeostasis in Consummatory Behavior", Pharmacology Biochemistry and Behavior, Nov. 2010, 97(1):47-54.

Ott, et al., "Oxytocin Reduces Reward-Driven Food Intake in Humans", Diabetes, Oct. 2013, 62(10):3418-3425.

Pollack, "Seeking Clues to Obesity in Rare Hunger Disorder: [Business/Financial Desk]", dated Jan. 16, 2014 (correction of Jan. 15, 2014 article), published on New York Times, Late Edition (East Coast) New York, N.Y (Jan. 15, 2014): B.1, [retrieved on Jan. 24, 2019]. Retrieved from the Internet: https://www.nytimes.com/2014/01/15/health/seeking-clues-to-obesity-in-rare-hunger-disorder.html.

Schaller, et al., "A single postnatal injection of oxytocin rescues the lethal feeding behaviour in mouse newborns deficient for the imprinted Mage12 gene", Human Molecular Genetics, Dec. 15, 2010, 19(24):4895-905.

Smith et al., "Prader-Willis Syndrome [PWS]—Is Behavioral Modification Possible? (abstract)", Twin Research and Human Genetics, Aug. 2011, 14(4):350-351.

Striepens et al., "Prosocial effects of oxytocin and clinical evidence for its therapeutic potential", Frontiers in Neuroendocrinology, Oct. 2011, 32(4):426-450.

Swaab, et al., "Neuropeptides in Hypothalamic Neuronal Disorders", Jeon, KW [Editor]. Int. Rev. Cytol., 2004, pp. 305-375.

"Search orphan drug designations and approvals." FDA, Date Designated: Apr. 11, 2014. Retrieved from the Internet: https://www.accessdata.fda.gov/scripts/opdlisting/oopd/detailedIndex.cfm?cfgridkey=423014.

University of Florida, "Oxytocin Trial in Prader-Willi Syndrome", NCT02013258 clinicaltrials.gov, [retrieved on Jul. 28, 2017]. Retrieved from the Internet: https://clinicaltrials.gov/ct2/show/NCT02013258.

University Hospital, "Tolerance of Intranasal Administration of OT in Prader-Willi Newborn Babies", NCT01548521 clinicaltrials.gov, [retrieved on Jul. 28, 2017]. Retrieved from the Internet: https://clinicaltrials.gov/ct2/show/NCT01548521.

University Hospital, "Evaluation of Tolerance, Suckling and Food Intake After Repeated Nasals Administrations of Oxytocin in PWS

(56) References Cited

OTHER PUBLICATIONS

Infants", NCT02205034 clinicaltrials.gov, [retrieved on Jul. 28, 2017]. Retrieved from the Internet: https://clinicaltrials.gov/ct2/show/NCT02205034.

University Hospital, "Comparative Study Between Prader-Willi Patients Who Take Oxytocin Versus Placebo", NCT01038570 clinicaltrials.gov, [retrieved on Jul. 28, 2017]. Retrieved from the Internet: https://clinicaltrials.gov/ct2/show/NCT01038570.

van Dongen et al., 1998, "Ascending dose tolerance study of intramuscular carbetocin administered after normal vaginal birth." Eur J Obstet Gynecol Reprod Biol. 77(2):181-7.

VerticalNews.com, "Prader-Willi Syndrome; Oxytocin promises hope in Prader-Willi syndrome", [retrieved on Jul. 17, 2011]. Retrieved from the Internet: https://dialog.proquest.com/professional/docview/875340097?accountid=156232.

World Health Organization, "Oxytocin draft proposal for The International Pharmacopoeia", Aug. 2007.

\* cited by examiner

METHOD OF TREATING PRADER-WILLI SYNDROME

CROSS-REFERENCE TO RELATED APPLICATION

This application claims priority under 35 U.S.C. § 119(e) to U.S. Provisional Application No. 62/052,957 filed Sep. 19, 2014, the disclosure of which is incorporated herein in its entirety.

SEQUENCE LISTING

The instant application contains a Sequence Listing which has been submitted electronically in ASCII format and is hereby incorporated by reference in its entirety. Said ASCII copy, created on Jul. 20, 2017, is named 27521-0078US1_SL.txt and is 11,810 bytes in size.

TECHNICAL FIELD

This disclosure relates to methods of treating Prader-Willi Syndrome, as well as related compositions.

BACKGROUND

Prader-Willi syndrome (PWS) is a genetic disorder that occurs in approximately one out of every 16,000 births. This rare complex and multisystem genetic disorder is caused by the lack of expression of paternally inherited imprinted genes on chromosome 15q11-q13 that may occur via one of three main mechanisms: paternal microdeletion, maternal uniparental disomy, and imprinting defect.

The course and natural history of PWS has classically been described as consisting of two distinct clinical stages, albeit current knowledge indicates these are more nuanced than originally thought. The first stage occurs during the neonatal and early infancy period, and is characterized by varying degrees of hypotonia, weak cry, poor suck reflex, feeding difficulties (failure to thrive), developmental delay, temperature instability, and underdeveloped sex organs (hypogonadism). Motor and language development delays are also notable during this first stage. The neonatal symptoms typically improve by 9-25 months of age, along with improved muscle tone, the child becomes more alert, and with more appropriate appetite.

The second stage of PWS (beginning ~2-4 years of age) is characterized by more rapid weight gain, onset and escalation of hyperphagia, and continued growth and developmental delays. In addition, as hyperphagia emerges, a separate and distinctly negative constellation of maladaptive or problematic behaviors is observed. These maladaptive (problematic) behaviors include temper tantrums, irritability, stubbornness, repetitive and compulsive behaviors, and aggression. External food limits and supervision are needed. Otherwise, individuals with PWS face the risk of life-threatening obesity. Once food-seeking behavior ensues, parents will generally implement food security, reduced caloric intake, and constant supervision at meals and around food access. Even with supervision, many persons with PWS are quite adept and clever in obtaining food. Obesity as a life-threatening condition and the concurrent, and often time severe maladaptive behavioral difficulties, are the central challenging issues for individuals with the syndrome and their families.

SUMMARY

This disclosure is based on the unexpected discovery that selective oxytocin receptor agonists can be effective in treating Prader-Willi Syndrome.

In one aspect, this disclosure features a method of treating Prader-Willi Syndrome that includes administering to a patient in need thereof an effective amount of a composition comprising a selective oxytocin receptor agonist or a pharmaceutically acceptable salt thereof.

Other features, objects, and advantages will be apparent from the description and the claims.

DETAILED DESCRIPTION

This disclosure generally relates to methods of treating Prader-Willi Syndrome that includes administering to a patient in need thereof an effective amount of a composition containing a selective oxytocin receptor agonist or a pharmaceutically acceptable salt thereof. The term "selective oxytocin receptor agonist" refers to a compound that has a greater agonist activity at a human oxytocin (hOT) receptor than at a human vasopressin receptor (e.g., a human V2 (hV2) receptor) and has a greater selectivity compared to oxytocin. As mentioned herein, agonist activity is expressed as $EC_{50}$, and selectivity is expressed as the ratio of $EC_{50}$ values (i.e., $EC_{50}$ hV2/$EC_{50}$ hOT). Oxytocin has a hV2/hOT selectivity ratio of 3 and carbetocin has a hV2/hOT selectivity ratio of 244. See Table 2 in WO2009/122285. In some embodiments, the selective oxytocin receptor agonist has a hV2/hOT selectivity ratio of at least 50 (e.g., at least 100, at least 200, at least 244, at least 300, at least 500, at least 1,000, at least 2,000, at least 3,000, at least 5,000, at least 10,000, at least 20,000, or at least 30,000). The term "an effective amount" refers to the amount of the composition that is required to confer a therapeutic effect on the treated subject.

In some embodiments, the selective oxytocin receptor agonist can be a compound of formula (I) (SEQ ID NO: 1):

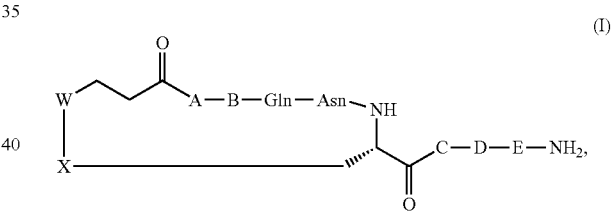

in which each of W and X, independently, is $CH_2$ and S, provided that W and X are not both $CH_2$; A is an amino acid selected from the group consisted of alanine substituted on the side chain with a 5- or 6-membered heteroaromatic ring; tyrosine; and phenylalanine substituted on the phenyl ring with halogen, $C_{1-4}$ alkoxy, $C_{1-4}$ alkylhydroxy, $C_{1-4}$ alkyl or amino; B is an amino acid selected from the group consisting of isoleucine; and glycine substituted on the α-carbon with $C_{4-6}$ cycloalkyl; C is an amino acid selected from the group consisting of proline, optionally substituted on the side chain (e.g., at the 4-position) with hydroxyl, $C_{1-4}$ alkoxy, halogen or azide, and proline having its side chain optionally interrupted by a heteroatom and which optionally interrupted side chain is optionally substituted with $C_{1-4}$ alkyl (e.g., at the 4-position); D is an amino acid selected from the group consisting of leucine; homoleucine; isoleucine; and glycine substituted on the α-carbon with $C_{4-6}$ cycloalkyl; and E is an amino acid selected from the group consisting of glycine and azaglycine.

The term "alkyl" refers to a saturated, linear or branched hydrocarbon moiety, such as $-CH_3$ or $-CH(CH_3)_2$. The term "cycloalkyl" refers to a saturated, cyclic hydrocarbon moiety, such as cyclohexyl. A five-membered heteroaromatic ring system refers to a monocyclic aromatic ring system having five ring atoms, wherein 1, 2, 3, or 4 ring atoms are independently selected from N, O, and S. Such ring systems can be, for example, thienyl, furyl, imidazolyl, pyrrolyl, pyrazolyl, thiazolyl, thiadiazolyl, or tetrazolyl. A six-membered heteroaromatic ring system refers to a monocyclic aromatic ring system having six ring atoms, wherein 1, 2, 3, or 4 ring atoms are independently selected from N, O, and S. Such ring systems can be, for example, pyridyl, pyrazinyl, pyrimidinyl, or pyridazinyl.

Substituent moieties can be, for example, halogen (fluorine, chlorine, or bromine) atoms, alkyl, cycloalkyl, hydroxy (OH), alkoxy (O-alkyl), alkylthio (—S— alkyl), alkylhydroxy (-alkyl-OH), azide (—$N_3$), amino (—NRR', wherein R and R' can be independently hydrogen or $C_{1-4}$ alkyl), or 5- or 6-membered heteroaromatic ring systems.

In some embodiments, referring to formula (I), when C is 4-hydroxyproline, A can be either phenylalanine substituted on the phenyl ring with halogen, or $C_{1-4}$ alkylhydroxy. In some embodiments, when C is 4-hydroxyproline and A is phenylalanine substituted on the phenyl ring with halogen, either B or D can be glycine substituted on the α-carbon with $C_{4-6}$ cycloalkyl, or D can be isoleucine.

In some embodiments, referring to formula (I), when A is phenylalanine substituted on the phenyl ring with $C_{1-4}$ alkyl or halogen, C can be proline or proline substituted on the side chain with halogen.

In some embodiments, referring to formula (I), when A is phenylalanine substituted on the phenyl ring with halogen, either B or D can be glycine substituted on the α-carbon with $C_{4-6}$ cycloalkyl, or D can be isoleucine.

In some embodiments, A in formula (I) can be 4-halophenylalanine, for example, Cpa (4-chlorophenylalanine); 4-bromophenylalanine. In some embodiments, A can be alanine substituted on the side chain with a 5- or 6-membered heteroaromatic ring, for example, Ala(2-Fur) (2-furylalanine); Ala(3-Fur) (3-furylalanine); 2-Thi (2-thienylalanine); 3-Thi (3-thienylalanine); 2- or 3-pyrrolylalanine; 2-, 3- or 4-pyridylalanine; 2-, 4- or 5-imidazolylalanine; 2-, 4- or 5-thiazolylalanine; and 2- or 5-thiadiazolyl; or 5-tetrazolyl. In some embodiments, A can be tyrosine or A can be phenylalanine substituted at the 4-position of the phenyl ring with $C_{1-4}$ alkoxy groups or with an amino group, for example, Tyr(Me) (4-methoxyphenylalanine); 4-ethoxyphenylalanine; Aph (4-aminophenylalanine); or 4-N,N-dimethylaminophenylalanine. In some embodiments, A can be phenylalanine substituted at the 4-position on the phenyl ring with $C_{1-4}$ alkylhydroxyl, $C_{1-4}$ alkyl or halo, for example, Phe(4-Et) (4-ethylphenylalanine); 4-methylphenylalanine; Phe(4-$CH_2OH$) (4-hydroxymethylphenylalanine); 4-hydroxyethylphenylalanine; Phe(Br) (4-bromophenylalanine); 4-chlorophenylalanine; or 4-fluorophenylalanine.

In some embodiments, B in formula (I) can be isoleucine, or is glycine substituted with $C_{4-6}$ cycloalkyl, such as Gly (cPe) (cyclopentylglycine), Gly(cBu) (cyclobutylglycine), or cyclohexylglycine.

In some embodiments, C in formula (I) can be proline, optionally substituted at the 4-position of the proline ring with hydroxy, $C_{1-4}$ alkoxy, halo, or azido groups, for example, Hyp (4-hydroxyproline); Hyp(Me) (4-methoxyproline); Pro(F) (4-fluoroproline); or Pro($N_3$) (4-azidoproline). In some embodiments, C can be proline interrupted in the proline ring with a heteroatom, and optionally substituted on the proline ring with $C_{1-4}$ alkyl, for example, Thz (4-thiaproline) or Dmt (5,5-dimethylthiaproline).

In some embodiments, D in formula (1) can be leucine, Hol (homoleucine), isoleucine, and glycine substituted with $C_{4-6}$ cycloalkyl, such as Gly(cPe) (cyclopentylglycine), Gly (cBu) (cyclobutylglycine), or cyclohexylglycine.

In some embodiments, E in formula (I) can be glycine or AzGly (azaglycine).

A subset of compounds of formula (I) are those in which W is $CH_2$ and X is S. In such embodiments, A can be phenylalanine substituted on the phenyl ring with $C_{1-4}$ alkoxy (e.g., phenylalanine substituted at the 4-position on the phenyl ring with $OCH_3$). An example of such a compound of formula (I) is carbetocin, in which W is $CH_2$, X is S, A is phenylalanine substituted at the 4-position on the phenyl ring with $OCH_3$, B is isoleucine, C is proline, D is leucine, and E is glycine.

Certain exemplary compounds of formula (I) include (SEQ ID NOS 2-25, respectively, in order of appearance):

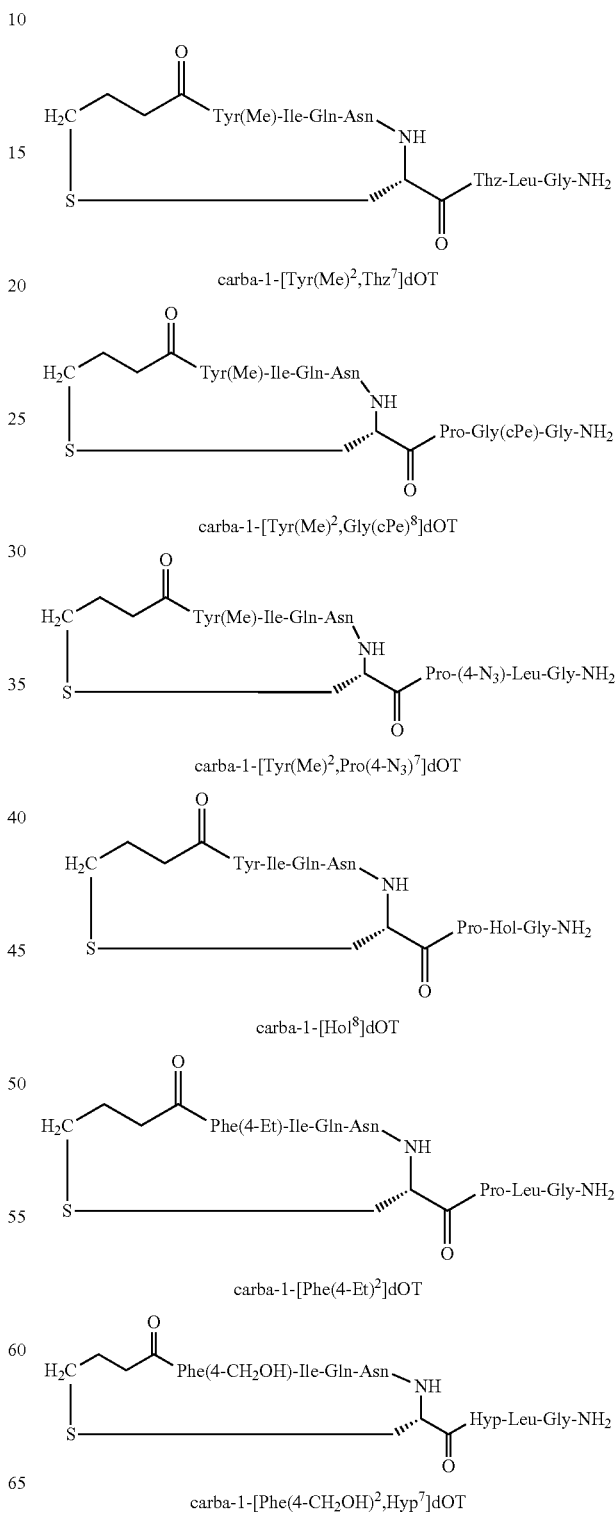

carba-1-[Tyr(Me)$^2$,Thz$^7$]dOT carba-1-[Tyr(Me)$^2$,Gly(cPe)$^8$]dOT carba-1-[Tyr(Me)$^2$,Pro(4-$N_3$)$^7$]dOT carba-1-[Hol$^8$]dOT carba-1-[Phe(4-Et)$^2$]dOT carba-1-[Phe(4-$CH_2OH$)$^2$,Hyp$^7$]dOT

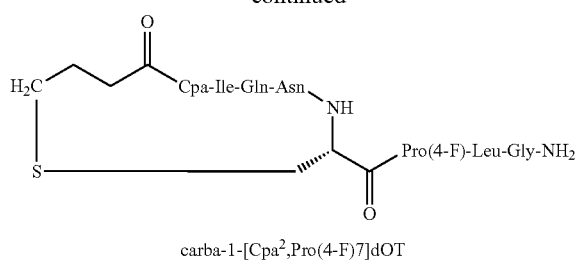
carba-1-[Cpa², Pro(4-F)⁷]dOT
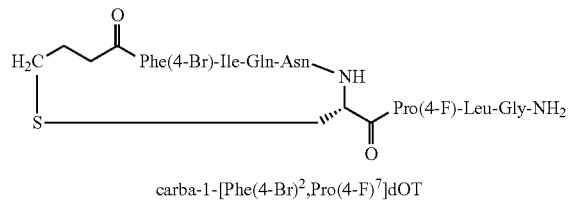
carba-1-[Phe(4-Br)², Pro(4-F)⁷]dOT
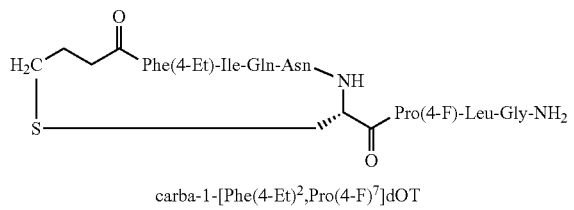
carba-1-[Phe(4-Et)², Pro(4-F)⁷]dOT
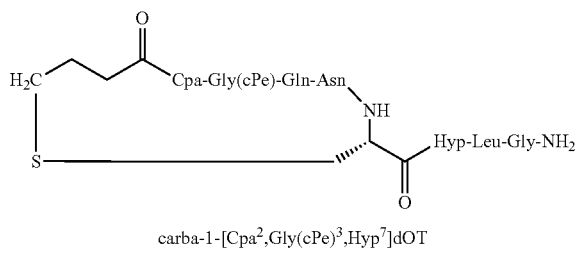
carba-1-[Cpa², Gly(cPe)³, Hyp⁷]dOT
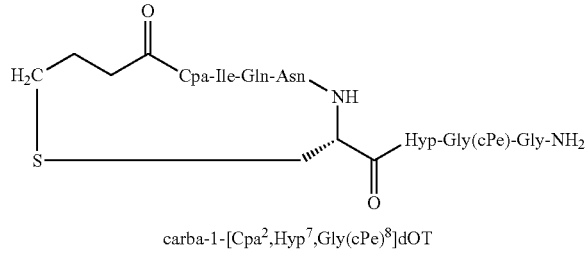
carba-1-[Cpa², Hyp⁷, Gly(cPe)⁸]dOT
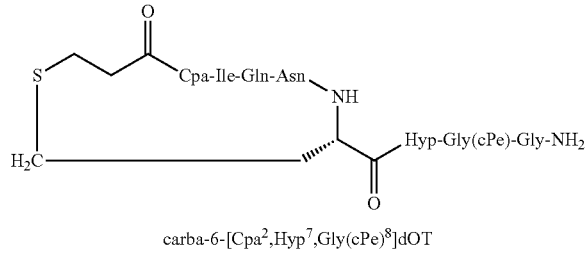
carba-6-[Cpa², Hyp⁷, Gly(cPe)⁸]dOT
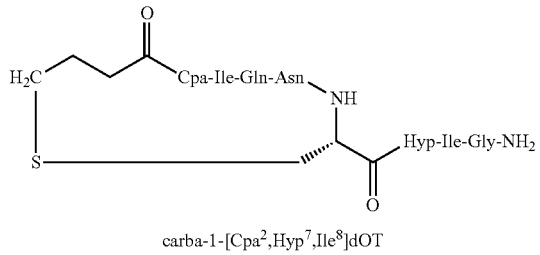
carba-1-[Cpa², Hyp⁷, Ile⁸]dOT
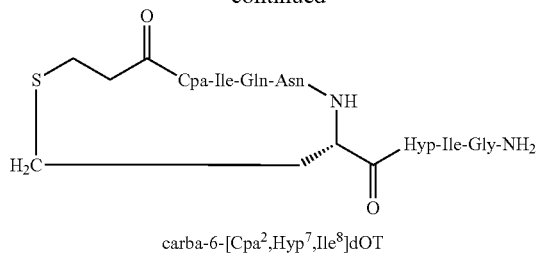
carba-6-[Cpa², Hyp⁷, Ile⁸]dOT
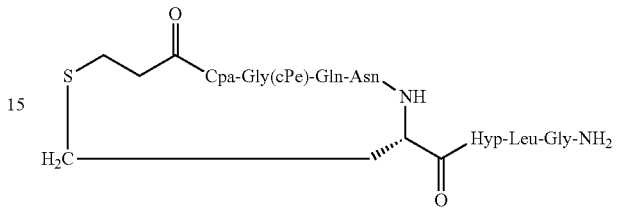
carba-6-[Cpa², Gly(cPe)³, Hyp⁷]dOT
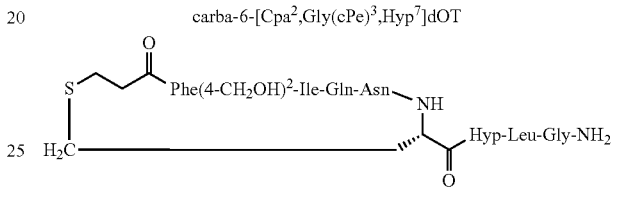
carba-6-[Phe(4-CH₂OH)², Hyp⁷]dOT
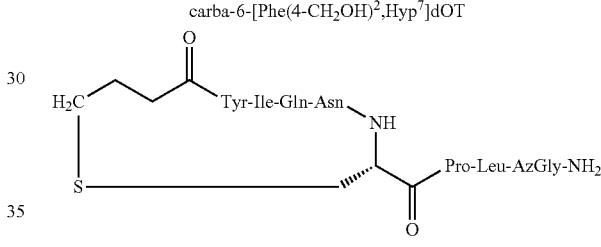
carba-1-[AzGly⁹]dOT
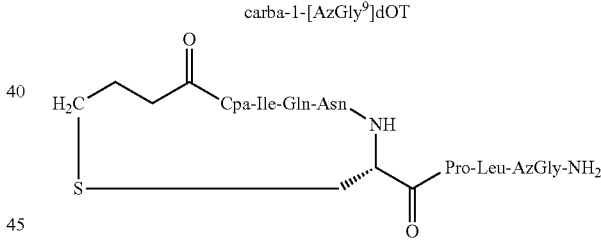
carba-1-[Cpa², AzGly⁹]dOT
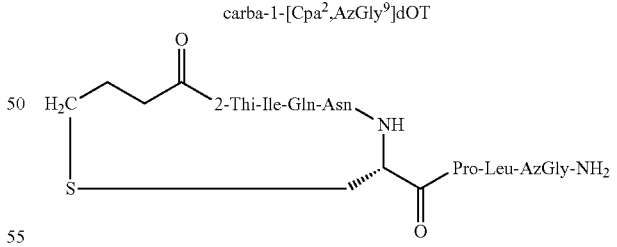
carba-1-[2-Thi², AzGly⁹]dOT
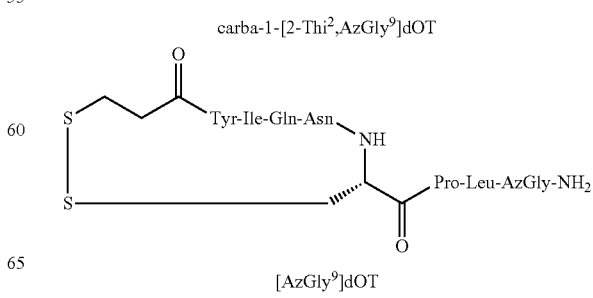
[AzGly⁹]dOT

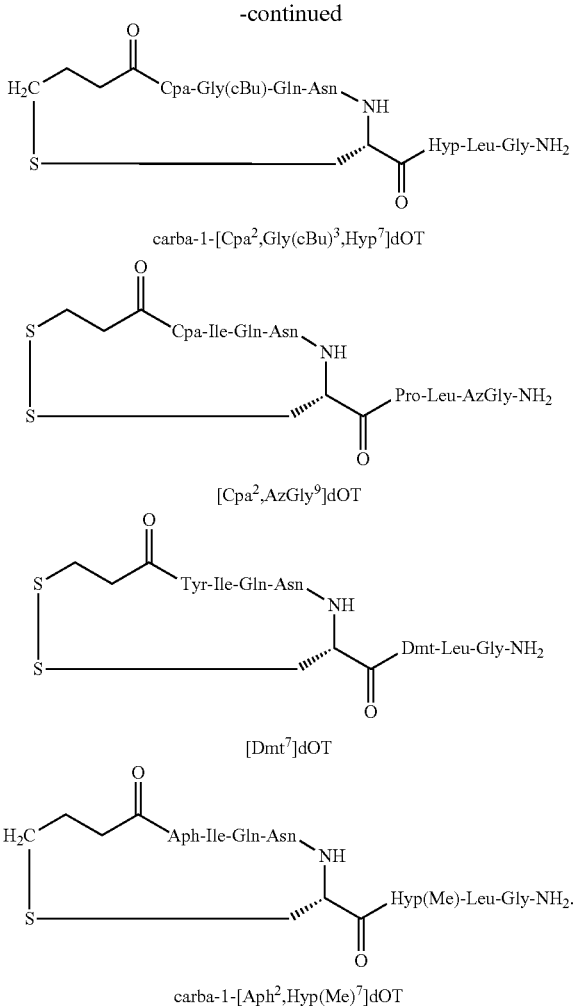

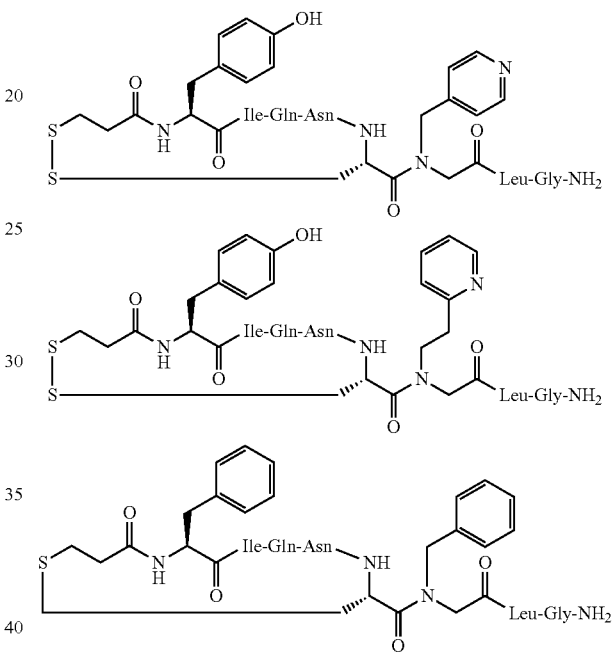

Substituent moieties for the groups in formula (II) can be selected from fluorine (F), chlorine (Cl) and bromine (Br) atoms and alkyl, hydroxy (OH), alkoxy (O-alkyl) and alkylthio (S-alkyl).

In some embodiments, when $R_2$ in formula (II) is H, p is 1, $R_3$ is H, n is 1 and W and X are both S, $R_1$ is not 4-hydroxyphenyl. In some embodiments, when $R_2$ is H, p is 0, $R_3$ is H, n is 1 and W and X are both S, $R_1$ is not 4-hydroxyphenyl. In some embodiments, a compound of formula (II) is not [1-β-Mpa,7-Sar]OT or deamino[7-glycine] oxytocin.

Certain exemplary compounds of formula (II) include (SEQ ID NOS 27-33, respectively, in order of appearance):

In some embodiments, the selective oxytocin receptor agonist is a compound of formula (II) (SEQ ID NO: 26):

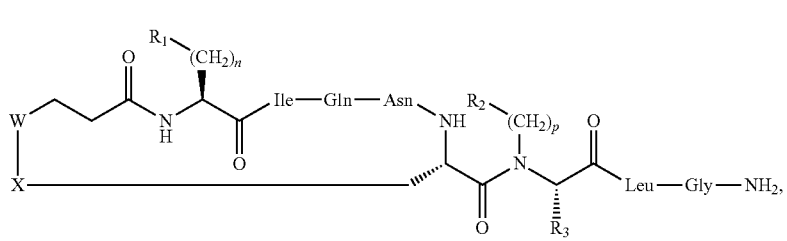

in which n is 0, 1 or 2; p is 0, 1, 2, 3, 4, 5 or 6; $R_1$ is aryl optionally substituted with at least one OH, F, Cl, Br, alkyl, or O-alkyl substituent; $R_2$ is $R_4$, H, alkyl, cycloalkyl, aryl, a 5-membered heteroaromatic ring system, or a 6-membered heteroaromatic ring system; $R_3$ is H or a covalent bond to $R_2$, when $R_2$ is $R_4$, to form a ring structure; $R_4$ is a $C_{1-6}$ alkylene moiety substituted with at least one O-alkyl, S-alkyl or OH substituent; each of W and X, independently, is $CH_2$ and S, provided that W and X are not both $CH_2$; alkyl is $C_{1-6}$ straight or $C_{4-8}$ branched chain alkyl and optionally has at least one hydroxyl substituent; aryl is unsubstituted or substituted phenyl; and cycloalkyl is $C_{3-6}$ cycloalkyl and optionally has at least one hydroxyl substituent.

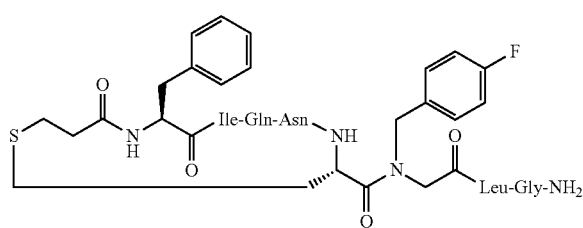

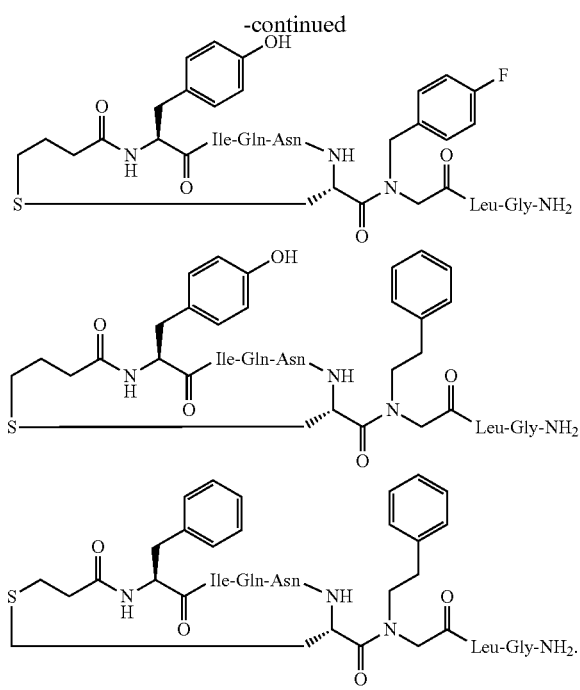

Other exemplary compounds of formulas (I) and (II) have been described, e.g., in WO 2011/035330 and WO 2009/122285, which are herein incorporated by reference.

This disclosure also features pharmaceutical compositions containing a therapeutically effective amount of at least one (e.g., two or more) of the selective oxytocin receptor agonists described above (e.g., compounds of formulas (I) and (II)) or a pharmaceutically acceptable salt thereof as an active ingredient, as well as at least one pharmaceutically acceptable adjuvant, diluent or carrier. Examples of pharmaceutically acceptable salts include acid addition salts, e.g. a salt formed by reaction with hydrohalogen acids (such as hydrochloric acid), mineral acids (such as sulphuric acid, phosphoric acid and nitric acid), and aliphatic, alicyclic, aromatic or heterocyclic sulphonic or carboxylic acids (such as formic acid, acetic acid, propionic acid, succinic acid, glycolic acid, lactic acid, malic acid, tartaric acid, citric acid, benzoic acid, ascorbic acid, maleic acid, hydroxymaleic acid, pyruvic acid, p-hydroxybenzoic acid, embonic acid, methanesulphonic acid, ethanesulphonic acid, hydroxyethanesulphonic acid, halobenzenesulphonic acid, trifluoroacetic acid, trifluoromethanesulphonic acid, toluenesulphonic acid, and naphthalenesulphonic acid).

The compounds of formulas (I) and (II) are either commercially available or can be made by methods known in the art, such as those described in WO 2011/035330 and WO 2009/122285, which are herein incorporated by reference.

The pharmaceutical composition described herein can optionally include at least one further additive selected from a disintegrating agent, binder, lubricant, flavouring agent, preservative, colourant and any mixture thereof. Examples of such and other additives can be found in "Handbook of Pharmaceutical Excipients"; Ed. A. H. Kibbe, 3rd Ed., American Pharmaceutical Association, USA and Pharmaceutical Press UK, 2000.

The pharmaceutical composition described herein can be adapted for oral, intravenous, intramuscular, topical, intraperitoneal, nasal, buccal, intraocular, intra-aural, sublingual or subcutaneous administration or for administration via the respiratory tract, e.g., in the form of an aerosol or an air-suspended fine powder. In some embodiments, the composition can be in the form of tablets, capsules, powders, microparticles, granules, syrups, suspensions, solutions, transdermal patches or suppositories.

In some embodiments, the pharmaceutical composition described herein can contain a selective oxytocin receptor agonist dissolved in an aqueous solution. For example, the composition can include a sodium chloride aqueous solution (e.g., containing 0.9 wt % of sodium chloride) to serve as a diluent.

In addition, this disclosure relates to use of a selective oxytocin receptor agonist as outlined above for, or for the manufacture of a medicament for, treatment of Prader-Willi Syndrome. Further, this disclosure relates to the use of a selective oxytocin receptor agonist as outlined above in, or in the manufacture of, a medicament for the treatment of Prader-Willi Syndrome.

The present disclosure further provides a composition comprising a selective oxytocin receptor agonist or a pharmaceutically acceptable salt thereof for (or for use in) the treatment of Prader-Willi Syndrome. The treatment of Prader-Willi Syndrome may be treatment to reduce hyperphagia and/or treatment to reduce obsessive compulsive behaviour.

The selective oxytocin receptor agonist is a compound that has a greater agonist activity at a human oxytocin (hOT) receptor than at a human vasopressin receptor (e.g., a human V2 (hV2) receptor) and has a greater selectivity compared to oxytocin. The agonist activity and selectivity may be measured by the method set out in WO2009/122285 (PCT/IB2009/005351). In this method, agonist activity of compounds on the hOT receptor is determined in a transcriptional reporter gene assay by transiently transfecting a hOT receptor expression DNA into a Chinese Hamster Ovary (CHO) cell line in concert with a reporter DNA containing intracellular calcium responsive promoter elements regulating expression of firefly luciferase. See Boss, V., Talpade, D. J., Murphy, T. J. *J. Biol. Chem.* 1996, May 3; 271(18), 10429-10432 for further guidance on this assay. Cells are exposed to serial dilutions of compounds diluted 10-fold per dose for 5 hours, followed by lysis of cells, determination of luciferase activity, and determination of compound efficacies and $EC_{50}$ values through non-linear regression. Oxytocin (OT) is used as an internal control in each experiment, and compounds are tested in at least three independent experiments. To determine selectivity, compounds are further tested in luciferase-based transcriptional reporter gene assays expressing the human vasopressin ($hV_2$) receptor. For further comparative purposes, carbetocin is also used as a reference compound. The $EC_{50}$ value given is the geometric mean expressed in nanomol/l (nM). Selectivity values are given as $EC_{50}$ ratios. Thus, agonist activity is expressed as $EC_{50}$, and selectivity may be expressed as the ratio of $EC_{50}$ values (i.e., $EC_{50}$ hV2/$EC_{50}$ hOT). Oxytocin has a hV2/hOT selectivity ratio of 3 and carbetocin has a hV2/hOT selectivity ratio of 244 (See Table 2 in WO2009/122285).

In some examples, the selective oxytocin receptor agonist has a hV2/hOT selectivity ratio of at least 50 (e.g., at least 100, at least 200, at least 244, at least 300, at least 500, at least 1,000, at least 2,000, at least 3,000, at least 5,000, at least 10,000, at least 20,000, or at least 30,000).

The selective oxytocin receptor agonist may be a compound of formula (I) (SEQ ID NO: 1):

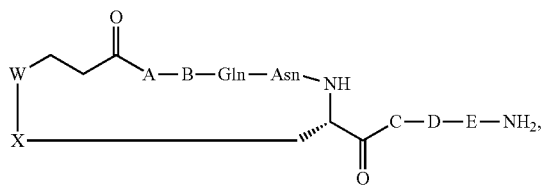

(I)

wherein
each of W and X, independently, is CH$_2$ and S, provided that W and X are not both CH$_2$;
A is an amino acid selected from the group consisted of alanine substituted on the side chain with a 5- or 6-membered heteroaromatic ring; tyrosine; and phenylalanine substituted on the phenyl ring with halogen, C$_{1-4}$ alkoxy, C$_{1-4}$ alkylhydroxy, C$_{1-4}$ alkyl or amino;
B is an amino acid selected from the group consisting of isoleucine; and glycine substituted on the α-carbon with C$_{4-6}$ cycloalkyl;
C is an amino acid selected from the group consisting of proline, optionally substituted on the side chain with hydroxyl, C$_{1-4}$ alkoxy, halogen or azide, and proline having its side chain optionally interrupted by a heteroatom and which optionally interrupted side chain is optionally substituted with C$_{1-4}$ alkyl;
D is an amino acid selected from the group consisting of leucine; homoleucine; isoleucine; and glycine substituted on the α-carbon with C$_{4-6}$ cycloalkyl; and
E is an amino acid selected from the group consisting of glycine and azaglycine.
In some examples, W is CH$_2$ and X is S. In some examples, A is phenylalanine substituted on the phenyl ring with C$_{1-4}$ alkoxy. In some examples, A is phenylalanine substituted at the 4-position on the phenyl ring with OCH$_3$. The compound of formula (I) may be carbetocin.

The selective oxytocin receptor agonist may be a compound of formula (II) (SEQ ID NO: 26):

alkyl is C$_{1-6}$ straight or C$_{4-8}$ branched chain alkyl and optionally has at least one hydroxyl substituent;
aryl is unsubstituted or substituted phenyl; and
cycloalkyl is C$_{3-6}$ cycloalkyl and optionally has at least one hydroxyl substituent.

The composition may be for use (in the treatment of Prader-Willi Syndrome) by intranasal administration. The composition may be for administration three times a day, for example wherein each administration delivers from about 1 mg to about 10 mg of the selective oxytocin receptor agonist, and/or wherein each administration is performed before a meal.

The composition may be for use (in the treatment of Prader-Willi Syndrome) wherein the treatment comprises administering a daily dose of from about 0.5 mg to about 30 mg of the selective oxytocin receptor agonist.

The composition may be for use (in the treatment of Prader-Willi Syndrome) wherein the treatment comprises administering a daily dose of from about 5.76 mg to about 28.8 mg of the selective oxytocin receptor agonist.

The composition may be for use (in the treatment of Prader-Willi Syndrome) wherein the treatment comprises administering a daily dose of from about 10 mg to about 28.8 mg of the selective oxytocin receptor agonist.

The composition may be for use (in the treatment of Prader-Willi Syndrome) wherein the treatment comprises administering a daily dose of about 28.8 mg of carbetocin.

The composition may be for use (in the treatment of Prader-Willi Syndrome) wherein the composition comprises an aqueous solution and the selective oxytocin receptor agonist is dissolved in the aqueous solution.

The composition may be for use (in the treatment of Prader-Willi Syndrome) wherein the composition comprises a sodium chloride aqueous solution.

The composition may be for use (in the treatment of Prader-Willi Syndrome) wherein the aqueous solution comprises about 0.9 wt % of sodium chloride.

The typical dosage of the selective oxytocin receptor agonists described herein can vary within a wide range and

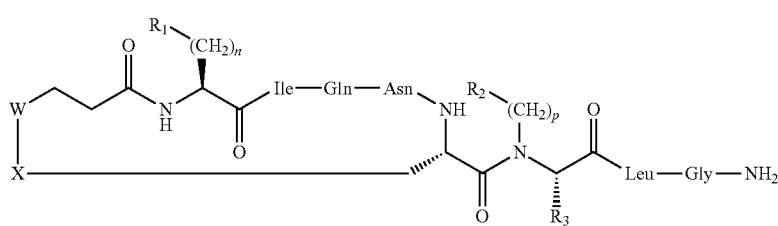

(II)

wherein
n is 0, 1 or 2;
p is 0, 1, 2, 3, 4, 5 or 6;
R$_1$ is aryl optionally substituted with at least one OH, F, Cl, Br, alkyl, or O-alkyl substituent;
R$_2$ is R$_4$, H, alkyl, cycloalkyl, aryl, a 5-membered heteroaromatic ring system, or a 6-membered heteroaromatic ring system;
R$_3$ is H or a covalent bond to R$_2$, when R$_2$ is R$_4$, to form a ring structure;
R$_4$ is a C$_{1-6}$ alkylene moiety substituted with at least one O-alkyl, S-alkyl or OH substituent;
each of W and X, independently, is CH$_2$ and S, provided that W and X are not both CH$_2$;

will depend on various factors such as the individual needs of each patient and the route of administration. Exemplary daily dosages can be at least about 0.5 mg (e.g., at least about 1 mg, at least about 5 mg, at least about 5.76 mg, at least about 10 mg, or at least about 15 mg) and/or at most about 30 mg (e.g., at most about 28.8 mg, at most about 25 mg, at most about 20 mg, or at most about 15 mg) of a selective oxytocin receptor agonist (e.g., carbetocin). The skilled person or physician may consider relevant variations to this dosage range and practical implementations to accommodate the situation at hand.

In some embodiments, the pharmaceutical composition described herein can be administered as an intranasal dosage form (e.g., a nasal spray). In such embodiments, the composition can be administered in a single dose or divided dosages, for example, into 1, 2 or 3 sub-doses (e.g., puffs) delivered to one or both nostrils. For example, the composition can be administered by delivering three puffs of a nasal spray into both nostrils such that each nostril receives a dose containing 1.6 mg of a selective oxytocin receptor agonist (e.g., carbetocin) in each puff. In such an example, each administration delivers a total of 9.6 mg of the selective oxytocin receptor agonist to a patient. In some embodiments, each administration of the composition can delivers at least about 1 mg (e.g., at least about 2 mg, at least about 3 mg, at least about 4 mg, or at least about 5 mg) and/or at most about 10 mg (e.g., at most about 9 mg, at most about 8 mg, at most about 7 mg, or at most about 6 mg) of the selective oxytocin receptor agonist to a patient.

In some embodiments, the pharmaceutical composition described herein can be administered once daily. In some embodiments, the pharmaceutical composition can be administered more than once daily (e.g., twice daily, three times daily, or four times daily).

In some embodiments, the pharmaceutical composition described herein can be administered before a meal. In some embodiments, the pharmaceutical composition described herein can be administered with or without food.

The contents of all publications cited herein (e.g., patents, patent application publications, and articles) are hereby incorporated by reference in their entirety.

The following examples are illustrative and not intended to be limiting.

Example: Clinical Trial of Using Carbetocin for Treating Patients Diagnosed with PWS Methodology A prospective, double-blind, placebo-controlled, parallel trial in subjects with PWS between 10 and 18 years of age with genetically confirmed diagnosis of PWS and a documented nutritional Phase 3 based on the criteria described in Miller et al, 2011 (Am J Med Genet A, 155A(5):1040-1049) was performed. The trial included a Screening Period, a 14-day Treatment Period, and a Follow-Up Period. Subjects, along with their parent/caregiver, were required to visit the investigational site 4 times over the course of the trial and participate in 2 phone call assessments. The trial schedule is listed below.

Visit 1: Screening Period (Day −7 to Day 0)
Visit 2: Baseline 1st day dosing on site (Day 1)
Visit 3: 2nd day dosing on site (Day 2)
Phone call assessment (Day 8±1)
Visit 4: End-of-Treatment Visit (Day 15)
Follow-up phone call (Day 19±3)

Following appropriate informed consent procedures, subjects underwent screening evaluations to determine eligibility before randomization. After randomization, efficacy measures and other assessments, including physical examination, vital signs, and collection of blood samples for clinical laboratory and pharmacokinetic evaluation, were performed at selected visits. Subjects were closely monitored for adverse events throughout the trial.

Prior to first dosing at the investigational site, parents/caregivers were trained on the proper use of the nasal spray device and procedures for investigational medicinal product (IMP) home delivery. Parents/caregivers were instructed to administer 3 intranasal spray pumps of blinded IMP per nostril 3 times daily before meals within the following intervals:

Morning dose: 06:00 a.m.-09:00 a.m.
Midday dose: 11:00 a.m.-1:00 p.m.
Evening dose: 4:30 p.m.-6:00 p.m.

Initial IMP dosing at Visit 2 (Day 1) and Visit 3 (Day 2) took place under observation of the site staff at the investigational site to ensure proper administration technique.

Number of Subjects 38 subjects, 10-18 years of age, with genetically confirmed diagnosis of PWS and documented nutritional phase 3 PWS criteria (based on Miller et al, 2011), were randomized. 36 subjects completed the study.

Selected Criteria Used for Inclusion/Exclusion

Inclusion Criteria:
1. Male or female 10-18 years of age (both inclusive).
2. Genetically confirmed diagnosis of PWS.
3. Nutritional Phase 3 PWS criteria based on Miller et al, 2011 (Am J Med Genet A, 155A(5):1040-1049).
4. Hyperphagia in Prader-Willi Syndrome Questionnaire-Responsiveness (HPWSQ-R) score greater than 13 at screening (Visit 1).

Exclusion Criteria:
1. Known genetic, hormonal, or chromosomal cause of cognitive impairment other than PWS.
2. Presence of currently active psychotic symptoms.
3. Presence of any cardiovascular disorders, epilepsy, frequent migraines or severe asthma.
4. Previous diagnosis of autism spectrum disorder by a qualified healthcare provider.
5. Nasal or sinus surgery within 1 year of screening (Visit 1).
6. Chronic sinusitis—more than 3 episodes per year.
7. Other nasal diseases that may affect deposition of intranasal medication.
8. Serum sodium <135 mmol/L at screening (Visit 1).

Medicinal Products

The IMPs used in this trial were carbetocin intranasal spray and placebo intranasal spray.

The carbetocin intranasal spray was prepared by dissolving 160 carbetocin in 0.9% sterile sodium chloride solution. Specifically, the preweighed carbetocin powder was reconstituted with the sodium chloride solution and subsequently transferred to a nasal spray device. Each spray pump actuation delivered a 50 µL volume of solution containing 1.6 mg carbetocin. Each dose consisted of 3 spray pump actuations in each nostril to deliver a total of 9.6 mg carbetocin. The daily dose of carbetocin was 28.8 mg.

The placebo intranasal spray was prepared by transferring a 0.9% sterile sodium chloride solution to a nasal spray device. Each spray pump actuation delivered 50 µL volume of the solution. Each dose consisted of 3 spray pump actuations in each nostril.

Endpoints

Primary Endpoint

The primary endpoint measured in this trial was change in the total score from Visit 2 to Visit 4 in Hyperphagia in Prader-Willi Syndrome Questionnaire-Responsiveness (HPWSQ-R), which was completed by the parent/caregiver.

Secondary Endpoints

Secondary endpoints of this trial were:
1. Clinical Global Impression-Improvement (CGI-I) after treatment at Visit 4.
2. Change from Visit 2 to Visit 4 for the following measurements:
HPWSQ-R hyperphagia behavior, drive, and severity domain scores.
Hyperphagia in Prader-Willi Syndrome Questionnaire-Responsiveness—completed by the clinician (HPWSQ-R-C) total score.

HPWSQ-R-C hyperphagia behavior, drive, and severity domain scores.

3. Change from Visit 1 to Visit 4 for the following measurements:
   Children's Yale-Brown Obsessive Compulsive Scale (CY-BOCS) score.
   Food Domain of the Reiss Profile.
4. Population PK/PD relationships for carbetocin.

Safety Endpoints:
Safety endpoints of this trial were:
Frequency, severity and seriousness of adverse events.
Clinically significant changes in vital signs.
Clinically significant findings during physical and laboratory assessments (e.g., physical examinations, including focused nasal examinations and nasal irritation).

Statistical Methods

The primary endpoint was analyzed using an analysis of covariance model with treatment and site as fixed effects and HPWSQ-R total score at Visit 2 (baseline) as a covariate. The last observation carried forward method was used to carry forward non-missing values of HPWSQ-R total score during the phone call assessment (Day 8±1) to impute missing values of HPWSQ-R total score at Visit 4. The treatment group difference in total score between placebo and carbetocin was calculated by subtracting the mean change from baseline in placebo from that in the carbetocin group. A borderline statistically significant difference at the 10% significant level was achieved if the upper limit of the 90% 1-sided confidence interval for the treatment difference was less than zero. The secondary endpoints were analyzed using a similar model to that of the primary endpoint.

Measurements Used in the Trial

Hyperphagia in Prader-Willi Syndrome Questionnaire-Responsiveness (HPWSQ-R)

The HPWSQ-R used in this trial was adapted from the Hyperphagia in Prader-Willi Syndrome Questionnaire (HPWSQ), an informant-based measure originally developed by Elisabeth Dykens (Vanderbilt) as a comprehensive tool to examine the psychological, developmental and neurobiological correlates of hyperphagia in PWS (Dykens et al., *Obesity.* 2007; 15:1816-26). HPWSQ-R represented all 11 items from the original HPWSQ and was structured to include a 1-week recall period. The HPWSQ-R was designed to be used for repeated measures to evaluate the change in hyperphagia severity after intervention. The HPWSQ-R was completed during Visits 1, 2, and 4 and on Day 8 of the trial by both the parent/caregiver (HPWSQ-R) and the clinician (HPWSQ-R-C).

Clinical Global Impression (CGI)

CGI rating scales are commonly used measures of symptom severity, treatment response and the efficacy of treatments in treatment studies of subjects with psychiatric, neurological or behavioral disorders. CGI is an overall clinician-determined summary measure that takes into account all available information including knowledge of the subject's history, psychosocial circumstances, symptoms, behavior, and the impact of the symptoms on the subject's ability to function. The CGI measures 3 components: 1) severity of illness, 2) global improvement, and 3) efficacy index (comparison of subject's baseline condition with a ratio of current therapeutic benefit to severity of side effects).

The CGI scale is a 7-point clinician rating of illness severity (CGI-S; 1=normal, not at all ill, 7=among the most extremely ill patients), at the beginning of the trial and a 7-point clinician rating of improvement of patient condition, during and at the end of the trial (CGI-I; 1=very much improved since baseline, 7=very much worse from baseline). (Busner and Targum, Psychiatry (Edgmont) 4:28-37. 2007). The CGI-S scale was completed during Visit 1, and the CGI-I scale was completed during Visit 4 and on Day 8 of the trial.

Children's Yale-Brown Obsessive Compulsive Scale (CY-BOCS)

The CY-BOCS is a clinician rated, semi-structured inventory of specific symptoms and symptom severity in pediatric obsessive-compulsive disorder (OCD). It includes 2 primary components: the Symptom Checklist and Severity Scale. The 10 severity items are summed to produce an Obsessions Severity Score (5 items), Compulsions Severity Score (5 items), and Total score (sum of all 10 severity items). CY-BOCS is well researched in psychometric studies with reported treatment sensitivity. CY-BOCS is described in more detail, e.g., in Scahill, et al., J Am Acad Child Adolesc Psychiatry, 36:844-52, 1997.

The CY-BOCS was completed at Visits 1 and 4 and on Day 8 of the trial.

Food Domain of the Reiss Profile

The food domain of the Reiss Profile consists of 7 questions that pertain to food seeking behavior and is described, e.g., in Dykens et al., *Am. J. Mental Retardation*, 1999, 104(2):158-169. The Food Domain of the Reiss Profile was completed at Visits 1 and 4 and on Day 8 of the trial.

Results

The results of the above clinic trials are summarized in Table 1 below.

TABLE 1

Efficacy Summary

| | Day 8 (Least-Squares Mean Change Carbetocin vs. Placebo/P-Value) | Day 15 (Least-Squares Mean Change Carbetocin vs. Placebo/P-Value) |
|---|---|---|
| HPWSQ-R | −5.2/0.0632 | −6.7/0.0290 |
| Behavior | −1.9/0.1153 | −2.0/0.1172 |
| Drive | −2.1/0.0625 | −1.6/0.1436 |
| Severity | −1.1/0.0572 | −1.5/0.0248 |
| HPWSQ-R-C | −10.2/0.0017 | −10.5/0.0014 |
| Behavior | −5.4/0.0017 | −4.3/0.0068 |
| Drive | −3.4/0.0019 | −2.6/0.0340 |
| Severity | −1.7/0.0061 | −2.2/0.0014 |
| Clinical Global Impression | −0.9/0.0162 | −0.8/0.0233 |
| CY-BOCS | −2.7/0.0956 | −6.2/0.0047 |
| Food Domain Score of Reiss Profile | −3.0/0.0184 | −4.4/0.0132 |

*Negative values indicate improvement in results for patients treated with carbetocin vs. placebo.

As shown in Table 1, patients treated with carbetocin exhibited statistically significant improvement ($P<0.05$) over placebo treated patients as demonstrated in the Day 15 results for HPWSQ-R, HPWSQ-R-C, CGI, CY-BOCS, and Food Domain Score of Reiss Profile.

Other embodiments are within the scope of the following claims.

What is claimed is:

1. A method of treating Prader-Willi Syndrome, comprising administering intranasally to a human patient in need thereof an effective amount of a composition comprising carbetocin or a pharmaceutically acceptable salt thereof, wherein the method comprises administering a daily dose of the carbetocin or pharmaceutically acceptable salt thereof of from about 5.76 mg to about 28.8 mg.

2. The method of claim 1, wherein the composition is administered three times a day.

3. The method of claim 2, wherein each administration delivers about 10 mg of the carbetocin or pharmaceutically acceptable salt thereof.

4. The method of claim 2, wherein each administration is performed before a meal.

5. The method of claim 1, wherein the method comprises administering a daily dose of the carbetocin or pharmaceutically acceptable salt thereof of from about 10 mg to about 28.8 mg.

6. The method of claim 1, wherein the method comprises administering a daily dose of about 28.8 mg of carbetocin or pharmaceutically acceptable salt thereof.

7. The method of claim 1, wherein the composition is administered as an intranasal spray.

8. The method of claim 3, wherein the composition is administered as an intranasal spray.

9. The method of claim 7, wherein the composition comprises the carbetocin or pharmaceutically acceptable salt thereof dissolved in an aqueous solution.

10. The method of claim 7, wherein the method comprises administering a daily dose of 28.8 mg of carbetocin.

11. The method of claim 7, wherein the method comprises administering a daily dose of about 10 mg of carbetocin or pharmaceutically acceptable salt thereof.

12. The method of claim 7, wherein the method comprises administering a daily dose of 10 mg of carbetocin.

13. The method of claim 2, wherein the method comprises administering a daily dose of 28.8 mg of carbetocin and wherein the composition is administered as an intranasal spray.

14. The method of claim 2, wherein the method comprises administering a daily dose of about 10 mg of carbetocin or pharmaceutically acceptable salt thereof and wherein the composition is administered as an intranasal spray.

15. The method of claim 2, wherein the method comprises administering a daily dose of 10 mg of carbetocin and wherein the composition is administered as an intranasal spray.

16. The method of claim 2, wherein the composition is administered as an intranasal spray.

17. The method of claim 5, wherein the composition is administered as an intranasal spray.

18. The method of claim 6, wherein the composition is administered as an intranasal spray.

19. The method of claim 11, wherein the composition comprises the carbetocin or pharmaceutically acceptable salt thereof dissolved in an aqueous solution.

20. The method of claim 18, wherein the composition comprises the carbetocin or pharmaceutically acceptable salt thereof dissolved in an aqueous solution.

21. The method of claim 9, wherein the composition comprises a sodium chloride aqueous solution.

22. The method of claim 21, wherein the aqueous solution comprises about 0.9 wt % of sodium chloride.

23. The method of claim 1, wherein the composition is in the form of a powder.

* * * * *

SEQUENCE LISTING

<160> NUMBER OF SEQ ID NOS: 33

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Alanine substituted on the side chain with a 5-
      or 6-membered heteroaromatic ring, tyrosine, or phenylalanine
      substituted on the phenyl ring with halogen, C1-4 alkoxy, C1-4
      alkylhydroxy, C1-4 alkyl or amino
<220> FEATURE:
<221> NAME/KEY: MOD_RES
<222> LOCATION: (3)..(3)
<223> OTHER INFORMATION: Isoleucine or glycine substituted on the alpha-
      carbon with C4-6 cycloalkyl
<220> FEATURE:
<221> NAME/KEY: MOD_RES
<222> LOCATION: (7)..(7)
<223> OTHER INFORMATION: Proline optionally substituted on the side
      chain (e.g., at the 4-position) with hydroxyl, C1-4 alkoxy,
      halogen or azide, or
<220> FEATURE:
<221> NAME/KEY: MOD_RES
<222> LOCATION: (7)..(7)
<223> OTHER INFORMATION: Cont'd from above: proline having its side
      chain optionally interrupted by a heteroatom and which optionally
      interrupted side chain is optionally substituted with C1-4 alkyl
      (e.g., at the 4-position)
<220> FEATURE:
<221> NAME/KEY: MOD_RES
<222> LOCATION: (8)..(8)
<223> OTHER INFORMATION: Leucine, homoleucine, isoleucine or glycine
      substituted on the alpha-carbon with C4-6 cycloalkyl
<220> FEATURE:
<221> NAME/KEY: MOD_RES
<222> LOCATION: (9)..(9)
<223> OTHER INFORMATION: Glycine or azaglycine
<220> FEATURE:
<223> OTHER INFORMATION: See specification as filed for detailed
      description of substitutions and preferred embodiments

<400> SEQUENCE: 1

Cys Xaa Xaa Gln Asn Cys Pro Xaa Xaa
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Tyr(Me)
<220> FEATURE:
<221> NAME/KEY: MOD_RES
<222> LOCATION: (7)..(7)
<223> OTHER INFORMATION: Thz

<400> SEQUENCE: 2

Cys Tyr Ile Gln Asn Cys Pro Leu Gly
1               5

<210> SEQ ID NO 3
<211> LENGTH: 9
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Tyr(Me)
<220> FEATURE:
<221> NAME/KEY: MOD_RES
<222> LOCATION: (8)..(8)
<223> OTHER INFORMATION: Gly(cPe)

<400> SEQUENCE: 3

Cys Tyr Ile Gln Asn Cys Pro Gly Gly
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Tyr(Me)
<220> FEATURE:
<221> NAME/KEY: MOD_RES
<222> LOCATION: (7)..(7)
<223> OTHER INFORMATION: Pro(4-N3)

<400> SEQUENCE: 4

Cys Tyr Ile Gln Asn Cys Pro Leu Gly
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Hol

<400> SEQUENCE: 5

Cys Tyr Ile Gln Asn Cys Pro Leu Gly
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Phe(4-Et)

<400> SEQUENCE: 6

Cys Phe Ile Gln Asn Cys Pro Leu Gly
1               5

<210> SEQ ID NO 7
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Phe(4-CH2OH)
<220> FEATURE:
<221> NAME/KEY: MOD_RES
<222> LOCATION: (7)..(7)
<223> OTHER INFORMATION: Hyp

<400> SEQUENCE: 7

Cys Phe Ile Gln Asn Cys Pro Leu Gly
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cpa
<220> FEATURE:
<221> NAME/KEY: MOD_RES
<222> LOCATION: (7)..(7)
<223> OTHER INFORMATION: Pro(4-F)

<400> SEQUENCE: 8

Cys Ala Ile Gln Asn Cys Pro Leu Gly
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Phe(4-Br)
<220> FEATURE:
<221> NAME/KEY: MOD_RES
<222> LOCATION: (7)..(7)
<223> OTHER INFORMATION: Pro(4-F)

<400> SEQUENCE: 9

Cys Phe Ile Gln Asn Cys Pro Leu Gly
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Phe(4-Et)
<220> FEATURE:
<221> NAME/KEY: MOD_RES
<222> LOCATION: (7)..(7)
<223> OTHER INFORMATION: Pro(4-F)
```

```
<400> SEQUENCE: 10

Cys Phe Ile Gln Asn Cys Pro Leu Gly
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cpa
<220> FEATURE:
<221> NAME/KEY: MOD_RES
<222> LOCATION: (3)..(3)
<223> OTHER INFORMATION: Gly(cPe)
<220> FEATURE:
<221> NAME/KEY: MOD_RES
<222> LOCATION: (7)..(7)
<223> OTHER INFORMATION: Hyp

<400> SEQUENCE: 11

Cys Ala Gly Gln Asn Cys Pro Leu Gly
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cpa
<220> FEATURE:
<221> NAME/KEY: MOD_RES
<222> LOCATION: (7)..(7)
<223> OTHER INFORMATION: Hyp
<220> FEATURE:
<221> NAME/KEY: MOD_RES
<222> LOCATION: (8)..(8)
<223> OTHER INFORMATION: Gly(cPe)

<400> SEQUENCE: 12

Cys Ala Ile Gln Asn Cys Pro Gly Gly
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cpa
<220> FEATURE:
<221> NAME/KEY: MOD_RES
<222> LOCATION: (7)..(7)
<223> OTHER INFORMATION: Hyp
<220> FEATURE:
<221> NAME/KEY: MOD_RES
<222> LOCATION: (8)..(8)
<223> OTHER INFORMATION: Gly(cPe)
```

```
<400> SEQUENCE: 13

Cys Ala Ile Gln Asn Cys Pro Gly Gly
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cpa
<220> FEATURE:
<221> NAME/KEY: MOD_RES
<222> LOCATION: (7)..(7)
<223> OTHER INFORMATION: Hyp

<400> SEQUENCE: 14

Cys Ala Ile Gln Asn Cys Pro Ile Gly
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cpa
<220> FEATURE:
<221> NAME/KEY: MOD_RES
<222> LOCATION: (7)..(7)
<223> OTHER INFORMATION: Hyp

<400> SEQUENCE: 15

Cys Ala Ile Gln Asn Cys Pro Ile Gly
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cpa
<220> FEATURE:
<221> NAME/KEY: MOD_RES
<222> LOCATION: (3)..(3)
<223> OTHER INFORMATION: Gly(cPe)
<220> FEATURE:
<221> NAME/KEY: MOD_RES
<222> LOCATION: (7)..(7)
<223> OTHER INFORMATION: Hyp

<400> SEQUENCE: 16

Cys Ala Gly Gln Asn Cys Pro Leu Gly
1               5

<210> SEQ ID NO 17
<211> LENGTH: 9
<212> TYPE: PRT
```

<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Phe(4-CH2OH)
<220> FEATURE:
<221> NAME/KEY: MOD_RES
<222> LOCATION: (7)..(7)
<223> OTHER INFORMATION: Hyp

<400> SEQUENCE: 17

Cys Phe Ile Gln Asn Cys Pro Leu Gly
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: AzGly

<400> SEQUENCE: 18

Cys Tyr Ile Gln Asn Cys Pro Leu Gly
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cpa
<220> FEATURE:
<221> NAME/KEY: MOD_RES
<222> LOCATION: (9)..(9)
<223> OTHER INFORMATION: AzGly

<400> SEQUENCE: 19

Cys Ala Ile Gln Asn Cys Pro Leu Gly
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: 2-Thi
<220> FEATURE:
<221> NAME/KEY: MOD_RES
<222> LOCATION: (9)..(9)
<223> OTHER INFORMATION: AzGly

<400> SEQUENCE: 20

Cys Ala Ile Gln Asn Cys Pro Leu Gly
1               5

```
<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: AzGly

<400> SEQUENCE: 21

Cys Tyr Ile Gln Asn Cys Pro Leu Gly
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cpa
<220> FEATURE:
<221> NAME/KEY: MOD_RES
<222> LOCATION: (3)..(3)
<223> OTHER INFORMATION: Gly(cBu)
<220> FEATURE:
<221> NAME/KEY: MOD_RES
<222> LOCATION: (7)..(7)
<223> OTHER INFORMATION: Hyp

<400> SEQUENCE: 22

Cys Ala Gly Gln Asn Cys Pro Leu Gly
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cpa
<220> FEATURE:
<221> NAME/KEY: MOD_RES
<222> LOCATION: (9)..(9)
<223> OTHER INFORMATION: AzGly

<400> SEQUENCE: 23

Cys Ala Ile Gln Asn Cys Pro Leu Gly
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Dmt
```

```
<400> SEQUENCE: 24

Cys Tyr Ile Gln Asn Cys Pro Leu Gly
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Aph
<220> FEATURE:
<221> NAME/KEY: MOD_RES
<222> LOCATION: (7)..(7)
<223> OTHER INFORMATION: Hyp(Me)

<400> SEQUENCE: 25

Cys Ala Ile Gln Asn Cys Pro Leu Gly
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<223> OTHER INFORMATION: See specification as filed for detailed
      description of substitutions and preferred embodiments

<400> SEQUENCE: 26

Cys Xaa Ile Gln Asn Cys Xaa Leu Gly
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Cys Tyr Ile Gln Asn Cys Gly Leu Gly
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Cys Tyr Ile Gln Asn Cys Gly Leu Gly
```

```
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Cys Phe Ile Gln Asn Cys Gly Leu Gly
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Cys Phe Ile Gln Asn Cys Gly Leu Gly
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Cys Tyr Ile Gln Asn Cys Gly Leu Gly
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Cys Tyr Ile Gln Asn Cys Gly Leu Gly
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Cys Phe Ile Gln Asn Cys Gly Leu Gly
1               5
```